United States Patent
Henry (10) Patent No.: US 11,744,739 B1
(45) Date of Patent: Sep. 5, 2023

(54) ADAPTIVE SIGNAL ROUTING IN A PERSONAL PROTECTIVE EQUIPMENT NETWORK

(71) Applicant: 3M INNOVATIVE PROPERTIES COMPANY, St. Paul, MN (US)

(72) Inventor: Paul D. Henry, Carmel, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 17/905,775

(22) PCT Filed: Mar. 1, 2021

(86) PCT No.: PCT/IB2021/051692
§ 371 (c)(1),
(2) Date: Sep. 7, 2022

(87) PCT Pub. No.: WO2021/181196
PCT Pub. Date: Sep. 16, 2021

Related U.S. Application Data (60) Provisional application No. 62/986,876, filed on Mar. 9, 2020.

(51) Int. Cl.
*A61F 11/14* (2006.01)
*A42B 3/30* (2006.01)
(Continued)

(52) U.S. Cl.
CPC .............. *A61F 11/145* (2022.01); *A42B 3/30* (2013.01); *A61F 11/08* (2013.01); *H04W 4/80* (2018.02)

(58) Field of Classification Search
CPC ........... A61F 11/145; A61F 11/08; A42B 3/30
See application file for complete search history.

(56) References Cited

U.S. PATENT DOCUMENTS

| | | | | |
|---|---|---|---|---|
| 4,374,301 A | * | 2/1983 | Frieder, Jr. ............... | A42B 3/30 379/430 |
| 5,404,577 A | * | 4/1995 | Zuckerman .............. | H04R 1/46 455/66.1 |

(Continued)

FOREIGN PATENT DOCUMENTS

| | | |
|---|---|---|
| WO | 2008033491 A2 | 3/2008 |
| WO | 2016089708 A1 | 6/2016 |
| WO | 2021064658 A1 | 4/2021 |

OTHER PUBLICATIONS

International Search Report for PCT International Application No. PCT/IB2021/051692, dated May 6, 2021, 4 pages.

*Primary Examiner* — David Bilodeau
(74) *Attorney, Agent, or Firm* — Katherine M. Scholz (57) ABSTRACT

A control unit for a worker wearing personal protective equipment is presented. The control unit includes a PPE network creator that, when activated, creates a network. The control unit also includes a PPE device identifier configured to detect a first PPE associated with the worker and a second PPE associated with the worker. The first PPE has a first speaker and a first microphone. The second PPE has a second speaker and a second microphone. The control unit also comprises a PPE network joiner that facilitates the first and second PPE joining the network. The control unit also comprises a preferred configuration selector that automatically selects a preferred speaker for the worker and a preferred microphone for the worker. The preferred speaker is the first or second speaker. The preferred microphone is the first or second microphone. The control unit also comprises a network communication component that automatically communicates a first device parameter settings to the first PPE and a second device parameter settings to the second PPE. The first and second device parameter settings are based on the selected preferred speaker and microphone.

20 Claims, 8 Drawing Sheets

(51) Int. Cl.
*A61F 11/08* (2006.01)
*H04W 4/80* (2018.01)

(56) References Cited

U.S. PATENT DOCUMENTS

| | | | | |
|---|---|---|---|---|
| 11,677,428 | B2* | 6/2023 | Ruttler | H04W 76/14 |
| | | | | 381/370 |
| 2006/0286933 | A1* | 12/2006 | Harkins | H04W 84/10 |
| | | | | 455/41.2 |
| 2014/0216447 | A1* | 8/2014 | Kihlberg | H04R 1/028 |
| | | | | 128/201.19 |
| 2015/0010158 | A1* | 1/2015 | Broadley | A61F 11/14 |
| | | | | 381/58 |
| 2017/0330444 | A1 | 11/2017 | M R et al. | |
| 2019/0070439 | A1 | 3/2019 | Namm | |
| 2021/0267300 | A1* | 9/2021 | Blomqvist | H04R 1/1041 |
| 2023/0114196 | A1* | 4/2023 | Reibner | A61F 11/12 |
| | | | | 455/518 |

\* cited by examiner

ADAPTIVE SIGNAL ROUTING IN A PERSONAL PROTECTIVE EQUIPMENT NETWORK

CROSS REFERENCE TO RELATED APPLICATIONS

This application is a national stage filing under 35 U.S.C. 371 of PCT/IB2021/051692, filed Mar. 1, 2021, which claims the benefit of U.S. Provisional Application No. 62/986,876, filed Mar. 9, 2020, the disclosure of which is incorporated by reference in its/their entirety herein.

BACKGROUND

There are many types of personal protective equipment. The personal protective equipment industry is increasingly providing new ways to protect workers in an environment. Many personal protective equipment articles include microphones or speakers.

SUMMARY

A control unit for a worker wearing personal protective equipment is presented. The control unit includes a PPE network creator that, when activated, creates a network. The control unit also includes a PPE device identifier configured to detect a first PPE associated with the worker and a second PPE associated with the worker. The first PPE has a first speaker and a first microphone. The second PPE has a second speaker and a second microphone. The control unit also comprises a PPE network joiner that facilitates the first and second PPE joining the network. The control unit also comprises a preferred configuration selector that automatically selects a preferred speaker for the worker and a preferred microphone for the worker. The preferred speaker is the first or second speaker. The preferred microphone is the first or second microphone. The control unit also comprises a network communication component that automatically communicates a first device parameter settings to the first PPE and a second device parameter settings to the second PPE. The first and second device parameter settings are based on the selected preferred speaker and microphone.

The above Summary is not intended to describe each illustrated embodiment or every implementation of the present disclosure. Further features and advantages are disclosed in the embodiments that follow. The Drawings and the Detailed Description that follow more particularly exemplify certain embodiments using the principles disclosed herein.

DETAILED DESCRIPTION

Many types of personal protective equipment (PPE) include a speaker, a microphone, or both. The speakers may provide a received audio transmission to a user, while the microphones may capture audio from the wearer. Different forms of PPE have different quality microphones and speakers. Additionally, wearing different PPE interferes with the ability of microphones to pick up audio, and for speakers to transmit audio. For example, a shoulder microphone may broadcast an incoming audio signal for a wearer. However, if the wearer is compelled to wear earplugs because of ambient noise, they will not hear the broadcast. Additionally, an over-the-ear headset may have a boom microphone, but if a user needs to also wear a respirator or mask, there may be interference and/or the wearer's voice may be muffled through the mask. Instead, in the first example, it would be better for audio to be transmitted through the earplugs and, in the second example, for a microphone in the mask to pick up audio instead of the boom microphone.

Currently, a wearer of PPE articles needs to manually turn on and off microphones and speakers to provide a preferred signal routing configuration. However, for workers who frequently need to swap PPE articles as they move between operations in a worksite, the need to manually switch can be an annoyance. It is desired to have a system that automatically, upon a PPE article entering or leaving a personal area network for a worker, to switch to a preferred signal routing configuration.

In U.S. Provisional patent application with Ser. No. 62/909,989, filed Oct. 3, 2019, incorporated herein by reference, the example of a dual hearing protection system was described in detail. A dual hearing protection system, as described herein, is one example scenario where signal routing is important. When both an in-ear and over-ear hearing protection unit are detected, a personal area network needs to adjust to reflect that the in-ear pieces will provide the final audio to a wearer, while the over-ear hearing protection unit will pick up audio signals from the wearer.

Active hearing protection includes one or more microphones that receive ambient sound from a user's surroundings and uses one or more speakers to play it back at a safe level. Active hearing protection devices use electronic circuitry to pick up ambient sound through the microphone and convert them to safe levels before playing it back to the user through a speaker. Additionally, active hearing protection may comprise filtering out undesired sound content, for example actively reducing the sound of a gunshot while providing human speech at substantially unchanged levels.

First, a sound signal is received by a microphone in an active hearing protection unit. The received sound signal is converted to an electronic signal for processing. After processing the sound signal such that all frequencies are at safe levels, the sound signal is reproduced and played back to a user through a speaker.

Some active hearing protection units are level dependent, such that an electronic circuit adapts the sound pressure level. Level dependent hearing protection units help to filter out impulse noises, such as gunshots from surrounding noises, and/or continuously adapt all ambient sound received to an appropriate level before it is reproduced to a user. Active hearing protection units, specifically level dependent active hearing protection units, may be necessary to facilitate communication in noisy environments, or environments where noise levels can vary significantly, or where high impulse sounds may cause hearing damage. A user may need to hear nearby ambient sounds, such as machine sounds or speech, while also being protected from harmful noise levels.

While active hearing protection units can be provided using either ear plugs or ear-muff designs, it may not be possible to provide sufficient protection using only one hearing protection device, e.g. ear plugs or ear-muffs. However, combining multiple hearing protection devices in an optimal fashion is not as simple as wearing both ear plugs and ear-muffs. Active hearing protection includes circuitry that is generally designed to operate independently from any other hearing device. For example, if an active hearing ear-muff set is not programmed for a user wearing passive ear plugs, it is possible that the user will not be able to hear the reproduced sound, which will make communication with others difficult.

Additionally, if a user wears both active ear plugs and active ear-muffs that are not aware of each other, it is likely that the ear plugs will operate as if receiving ambient sound and further process sound already processed by the earmuffs, resulting in distorted sound. In addition to the sound not being natural, overly distorted sound can cause nausea and discomfort to a user.

If used together, the speaker of a traditional level dependent earmuff will no longer deliver sound directly to the ear canal, as it was designed, which will also distort the acoustic experience. Additionally, the two-level dependent functions of the earmuff and earplug will be cascaded, with the acoustic output of the earmuff exciting the acoustic input of the level dependent earplug, resulting in an unpredictable steady-state and transient behavior.

The problem is further complicated as additional PPE articles are added to the combination. For example, a shoulder microphone can produce sound, but may not be audible once a user puts on and activates the dual hearing protection unit. Additionally, a respirator will interfere with a boom microphone of the over-the-ear headset picking up audio.

A system is desired that allows for multiple PPE articles to be used simultaneously. The system needs to detect each PPE article as it enters a network and determine whether the new PPE article is a preferred PPE article for either receiving audio from a wearer or providing audio to the wearer.

Figure 1:
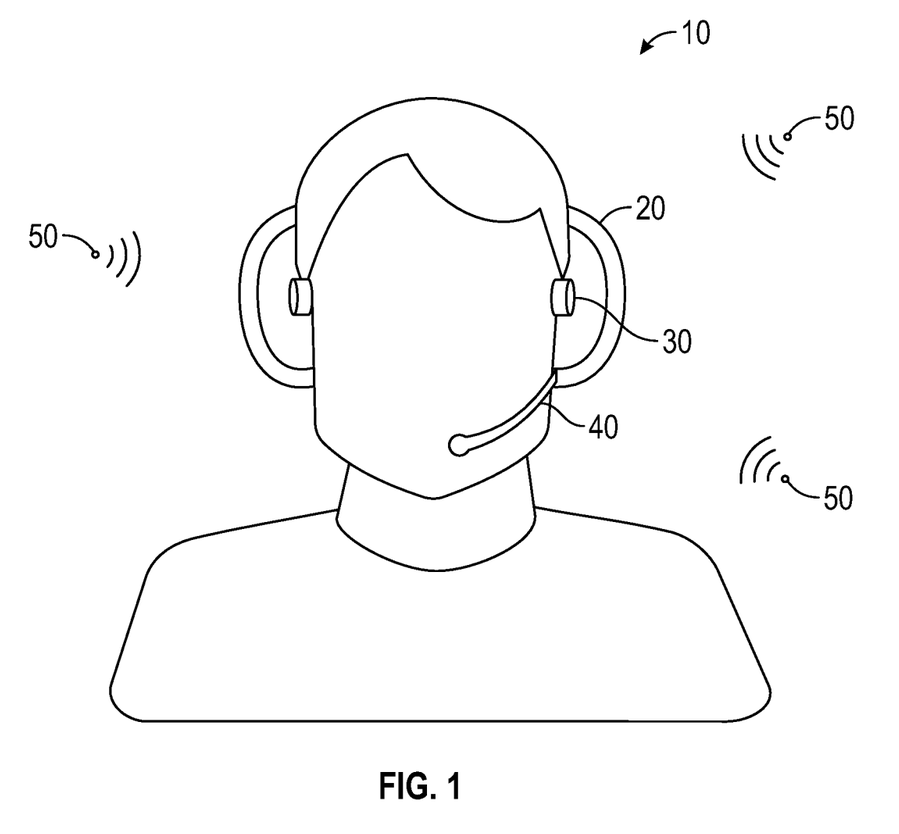
FIG. 1 illustrates a dual hearing protection system in accordance with an embodiment of the present invention.

FIG. 1 illustrates a dual hearing protection system in accordance with an embodiment of the present invention. A person 10 may be in an environment with a plurality of sounds 50. As illustrated in FIG. 1, different sounds 50 may have different noise levels associated with them. Some of noises 50 may be safe to hear at ambient levels, while others are not. In fact, some of sounds 50 may be loud enough that a single hearing protection system is not sufficient to bring them to safe levels.

In one embodiment, person 10 wears both a first hearing protection system 20 and a second hearing protection system 30. First hearing protection system 20 is illustrated as a pair of earmuffs while second hearing protection system 30 is illustrated as a pair of in-ear plugs. First and second hearing protection systems 20, 30 are both active hearing protection systems that are configured to detect each other and, once detected, enter a dual protection mode. While both first and second hearing protection systems 20, 30 are configured to operate as independent level-dependent hearing protection systems, they are also configured to enter a dual protection mode and coordinate hearing protection functionality.

In a dual protection mode, ambient sounds 50 may first be received by first hearing protection system 20. First hearing protection system 20 may conduct a first processing operation and produce a first processed sound. The first processed sound is received by second hearing protection system 30, which conducts a second processing operation to produce a second processed sound, which is provided to user 10. As described herein, 'first processed sound' refers to first hearing protection system 20 providing either an electronic signal directly to the earplug, or providing a sound signal through a speaker which is then picked up by the earplug.

In order for the second processed sound to sound natural to user 10, it is important for first and second hearing protection systems 20, 30 to be aware of each other, and to be programmed to operate in series to achieve additional hearing protection. As described below in greater detail, hearing protection systems 20 and 30 are both configured such that they can detect that another hearing protection system is available and enter a dual protection mode. In the dual protection mode, each of first and second hearing protection systems adjust their operation parameters to compensate for the presence of another hearing protection system. This helps to reduce distortion and other undesired audio artifacts, such as sound pumping, for example. For example, second hearing protection system 30 operates with the awareness that it is receiving a first processed sound signal, not an ambient sound 50, which can reduce distortion that would otherwise be experienced by using two active hearing protection units.

A dual hearing protection system can also include one or more microphones 40. Microphone 40 is illustrated in FIG. 1 as positioned to pick up the voice of user 10. However, other microphones (not shown) may be positioned to pick up ambient sounds 50. Additionally, each of first and second hearing protection systems 20, 30 may have one or more of their own microphones 40.

Figure 2:
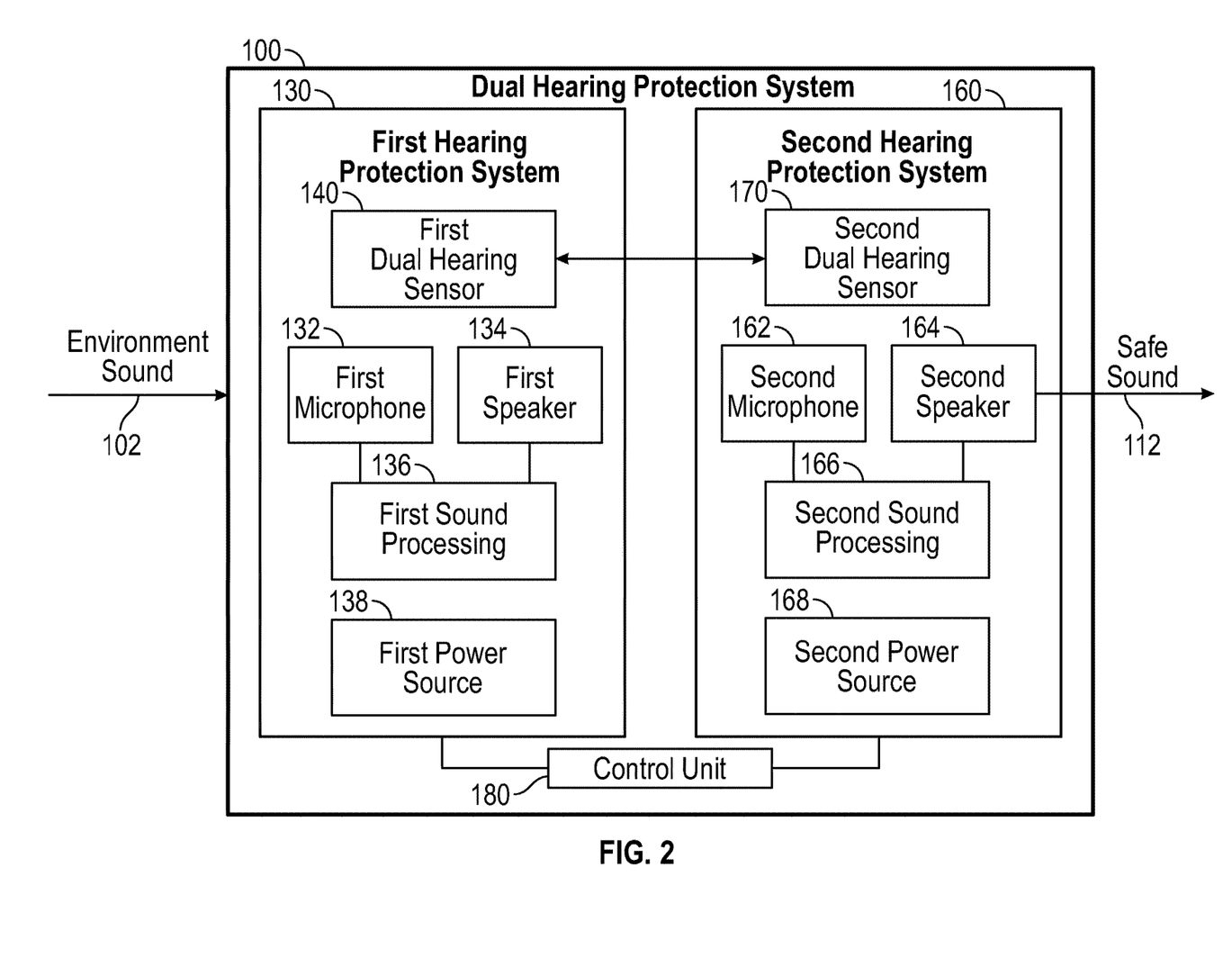
FIG. 2 is a block diagram of a dual hearing protection system in accordance with an embodiment of the present invention.

FIG. 2 is a block diagram of a dual hearing protection system in accordance with an embodiment of the present invention. System 100 may be used in conjunction with other PPE devices. Control unit 180 may have a stored preference list for PPE articles depending on different combinations of PPE articles that a user wears. For example, if a respirator is detected, it may be preferred for a microphone in the respirator to be used. Similarly, if in-ear plugs are detected, it may be preferred for the in-ear plugs to deliver an audio signal to a user. Preference may be based on preserving signal quality, reducing interference, or providing the most noise reduction. The example of dual hearing protection is illustrated in FIG. 2, however it is expressly contemplated, as discussed in greater detail below, that similar concepts can be extended to additional PPE articles.

System 100 is configured to receive ambient sound 102 from the environment, which may include sustained or impulse sounds at an unsafe level, and communicates sound 112 at a safe level to a user. System 100 includes a first hearing protection system 130 and a second hearing protection system 160, each of which are configured to operate independently. However, in one embodiment, both first and second hearing protection systems 130, 160 are also configured to operate in a dual protection mode.

First hearing protection system 130 includes a first microphone 132 and a first speaker 134. First microphone is configured to receive environmental sounds 102 from around a user. Received environment sounds 102 are converted to an electrical signal, which is then provided by microphone 132 to first sound processor 136. The electronic signal is then compressed by sound processor 136 according to a compression curve such that safe level sounds are still presented at a safe level, and sounds that are too loud are compressed. In some embodiments, some safe level sounds are actually amplified. The processed electronic signal is then converted back to a sound signal, which is provided to a user by a first speaker 134. The compression curves used by each of the first and second hearing systems are different when they operate in the dual protection mode than when they operate in an independent mode.

First hearing system 130, in one embodiment, also has a dual hearing sensor 140, which is configured to detect second hearing system 160. For example, dual hearing sensor 140 may detect a corresponding dual hearing sensor 170 of second hearing system 160, in one embodiment. In another embodiment, sensor 140 is not physically a part of first hearing system 130, but is instead part of another device configured to detect the presence of both first and second hearing systems 130, 160, and provide instructions for first and second hearing systems 130, 160 to enter a dual hearing protection mode. Once second hearing protection system 160 is detected, however, dual hearing sensor 140 may send a command for first hearing protection system 130 to sound processor 136. In an independent mode, sound processor 136 may use a first set of level dependent functions to adjust received sounds 102 to a safe sound level. However, in a dual protection mode, sound processor 136 may use a second set of level dependent functions to adjust received sounds 102 for provision to second hearing protection system 160. For example, a first compression curve, part of the first level dependent function set, may differ from a second compression curve, part of the second level dependent function set. Additional level dependent functionality that may change between the independent and dual hearing protection mode may include equalization, frequency response or other noise reduction functionality.

Second hearing protection system 160 has a second microphone 162 and a second speaker 164. Second microphone 162 is configured to receive processed sound from first speaker 134. Second microphone 162 converts the received processed sound to an electrical signal and provides it to second sound processing unit 166. Second sound processing unit 166 performs a second compression on the sound signal, which is converted to a safe sound signal 112 and provided to a user by second speaker 164. Second hearing protection system 160 is configured to operate in either an independent mode, as a sole hearing protection device, or in a dual hearing protection mode, in conjunction with first hearing protection system 130. Switching second hearing protection system 160 from an independent mode to a dual hearing protection mode is accomplished when dual hearing sensor 170 senses first hearing protection system 130 is also in operation. When operating in a dual hearing protection mode, second sound processing unit 166 uses a different compression curve than when operating in an independent mode. The dual protection mode compression curve used by second sound processor 166 takes into account the compression curve used by first sound processing system 136, such that safe sound 112 is natural and has reduced distortion than if first and second hearing protection systems 130, 160 operated independently.

In one embodiment, both first and second hearing protection systems 130, 160 are level dependent. Both first and second hearing protection systems 130, 160 have a power source, 138 and 168 respectively. However, while power sources 138 and 168 are illustrated as independent power sources, it is also contemplated that a single source could power both first and second hearing protection systems 130, 160.

In one embodiment, a control unit 180 is configured to create a network, detect both first and second hearing protection systems 130, 160 and facilitate their joining to the network and, over the network, provide the command to enter a dual protection mode for the dual hearing sensors 140, 170. However, while control unit 180 is illustrated as a separate device for clarity, it is contemplated that any of the PPE articles worn by a user could comprise the control unit, such that one PPE article sends the command to each other PPE system. In one embodiment, the command also includes the compression curve to use in the dual hearing protection mode.

While systems 130, 160 are described as single units, it is also expressly contemplated that each comprises two hearing protection units—for example, first hearing protection system 130 can comprise a set of ear muffs configured to be worn over a user's ears, while second hearing protection system 160 can comprise a set of ear plugs, configured to be worn within a user's ears. In the embodiment where second hearing protection system 160 comprises two unconnected ear plugs, it is contemplated that control unit 180 could be located in any of the ear-muffs, the left ear plug, or the right ear plug.

Figure 3:
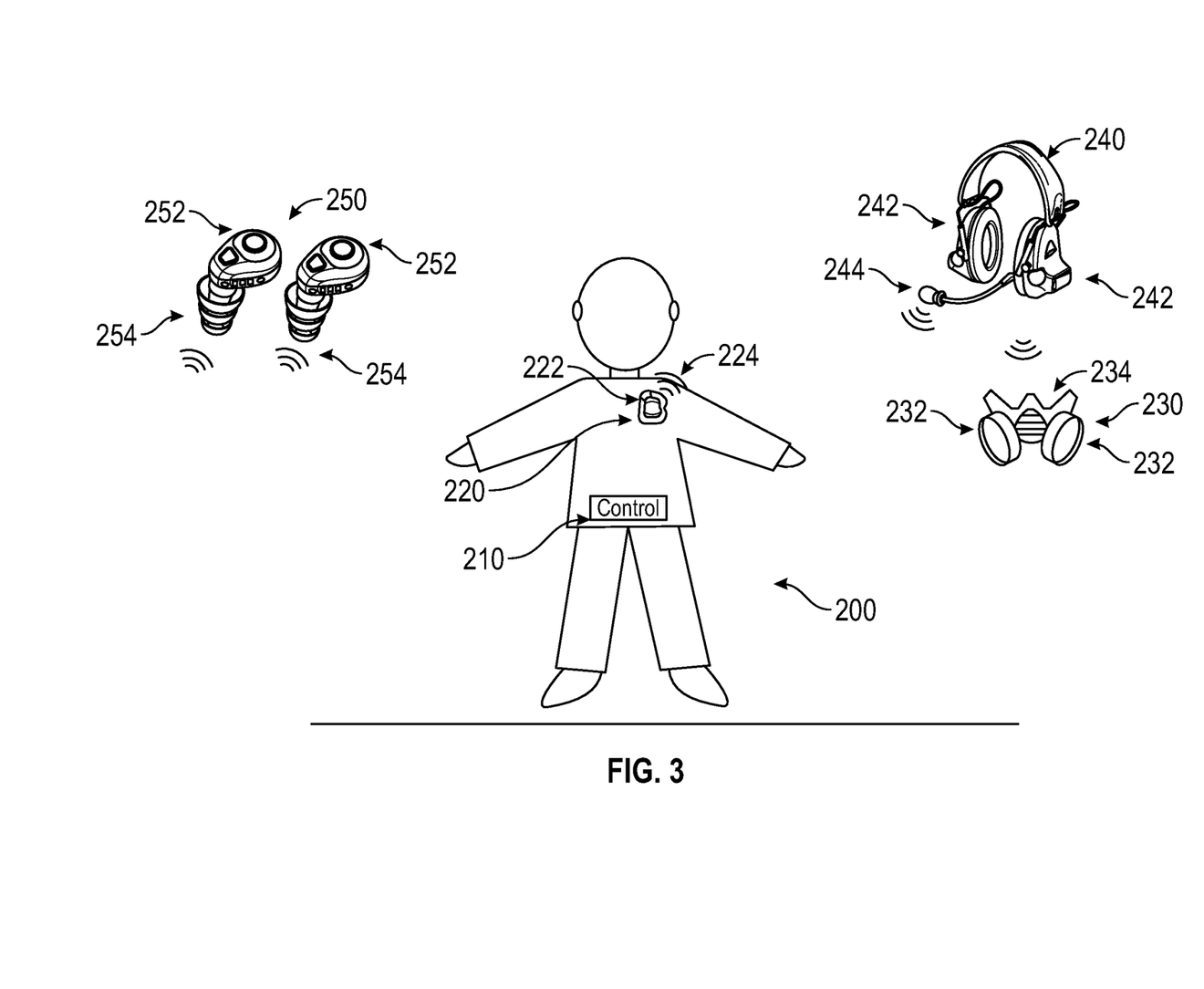
FIG. 3 illustrates a diagram of a PPE system in accordance with an embodiment of the present invention.

FIG. 3 illustrates a diagram of a PPE system in accordance with an embodiment of the present invention. PPE system is worn by a worker 200, who may need one or more PPE articles for a given operation, or in a given work environment.

PPE system includes a master device 210, which is in charge of forming a PPE network and accepting new PPE articles into the network. Master device 210 is also responsible for determining which functionality of each new PPE articles are automatically turned on or off based on other PPE articles already in the network. For example, it is important that only one microphone is active in a PPE network, even though multiple PPE articles in the network may have microphone functionality. If multiple microphones are active, it can create feedback in an audio stream. Additionally, it is desired that master device 210 be responsible for automatically selecting a preferred microphone to keep functional, and turning off functionality of non-preferred microphones. This can prevent a user 200 from having to remove at least some PPE to readjust settings. For example, if both in-ear hearing protectors 250 and over-ear headphones have a microphone, and user 200 forgets to turn off the microphone feature for in-ear hearing protectors when putting them on, the problem may only be realized when user 200 speaks. User 200 may then need to remove hearing protector 240 in order to be able to access microphones 254. If user 200 is using a dual hearing protection mode of operation, this may cause user 200 to be exposed to loud sounds that are not processed by headset 240 while microphone 254 is being turned off. In addition to taking additional time away from an operation, this could cause hearing damage to wearer 200.

Master device 210 may allow different PPE articles 220, 230, 240 and 250 to enter and leave a network as wearer 200 needs or stops needing them, depending on an environment. For example, a police officer may respond to a scene with a shoulder microphone 220, which has a speaker 222 to broadcast sound to officer 200 and a microphone 224 which receives audio from officer 200.

Officer 200 may need to put in in-ear hearing protector 250, for example if incoming audio includes sensitive information that bystanders should not hear, or if a situation gets loud enough that hearing protection may be needed. Each in-ear hearing protector 250 may have a microphone 252 for picking up speech from officer 200 and a speaker 254 for broadcasting sound in an ear of wearer 200. When master device 210 detects devices 250, and allows them to join a PPE network, it may determine that incoming audio should be presented to officer 200 through in-ear devices 250. However, microphone 222 of shoulder microphone may be better suited to picking up speech from wearer 200. So master device 210 may allow devices 250 to join the network and automatically switch on speakers 254, switch off microphones 252 and switch off speaker 224. The transition may happen seamlessly, so that officer 200 does not experience a lapse in incoming audio.

Additional hearing protection may be needed, for example if officer 200 is in a very loud area where dual hearing protection is needed. Officer may then need to add over-the-ear protection device 240, which also has a microphone 244 and speakers 242. Master device 210 may, upon detecting that device 240 is available for joining the network, determine that dual hearing protection mode is desired and set up dual hearing protection, as described above. Additionally, master device 210 may also cause incoming audio to be routed directly to speakers 254, as incoming audio may not need to be processed through dual hearing protection with ambient noise. Additionally, master device 210 may determine that a microphone 244 is better suited for picking up speech from officer 200, as it is closer to the mouth of wearer 200 and, therefore, less likely to pick up interference. A microphone 222, therefore, is turned off when over-the-ear headset 240 joins the network and microphone 244 is turned on. Again, the transition occurs seamlessly so that officer 200 experiences substantially no interruption in incoming or outgoing audio.

Officer 200 may also need to enter a potentially unsafe area that requires the use of a respirator 230. For example, a smoke or gas-filled area with compromised air. Device 210 may detect that respirator 230 is available to join the network and has a microphone 234 that can pick up speech from officer 200, and speakers 232 that can broadcast incoming sound. While microphone 234 may be better suited to pick up audio from officer 200 than microphone 244, because respirator 230 will interfere with speech sounds picked up by microphone 244, many respirators are still lacking good speaker quality for speakers 232. Additionally, if dual hearing protection is still needed, and devices 250 and 240 are still in the PPE network, it is preferred for incoming audio to still be routed to in-ear hearing protection devices. So, speakers 254 remain activated, microphone 244 is turned off, and microphone 234 is turned on.

Described with respect to FIG. 3 is one example scenario where PPE devices enter a network created and maintained by control device 210. However, it is expressly contemplated that other PPE devices not illustrated in FIG. 3 may enter or join a network, and that not all articles illustrated in FIG. 3 may be present for every scenario that officer 200 may enter.

Figure 4:
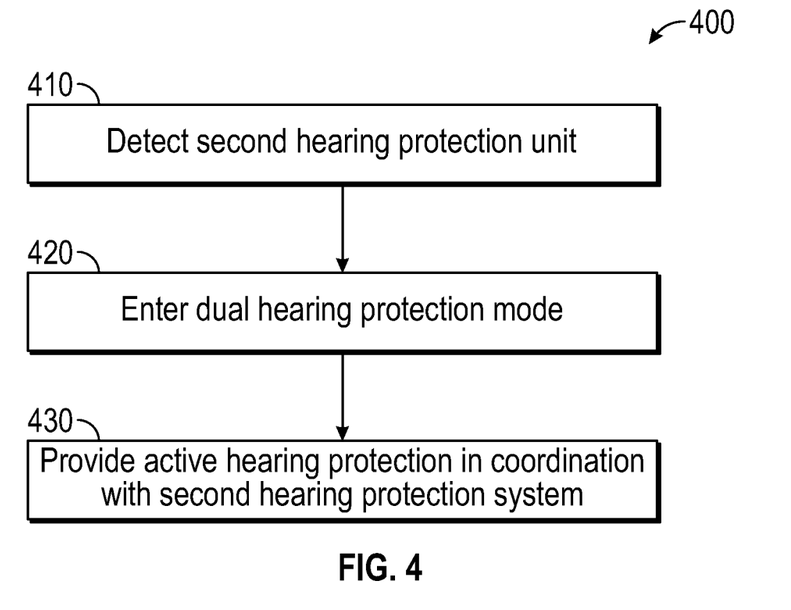
FIG. 4 illustrates a method of entering a dual hearing protection mode for a system of hearing protection units.

FIG. 4 illustrates a method of entering a dual hearing protection mode for a system of hearing protection units. FIG. 4 illustrates a method of entering a dual hearing protection mode for a system of hearing protection units. Method 400 may be useful, for example, for two level-dependent hearing protection systems that are configured to operate either in an independent mode or in a dual protection mode.

In block 410, a first hearing protection system detects a second hearing protection system. First and second hearing protection systems may be selected from either an active ear plug hearing protection system or an active ear-muff hearing protection system. Detection may comprise a first hearing protection system directly detecting the presence of the second hearing protection system, in one embodiment. In another embodiment, detection may comprise a first hearing protection system detecting a network and, through the network, becoming aware of a second hearing protection system.

In block 420, both first and second hearing protection systems enter a dual hearing protection mode. For example, each system may be configured, after powering up, to operate in an independent mode and only enter a dual protection mode when a second hearing protection system is detected. Alternatively, each system may be configured, after powering up, to search for and enter a dual protection mode if a second hearing protection system is found.

In block 430, active hearing protection is provided to a user. In one embodiment, both first and second hearing protection systems are configured to perform a level dependent operation on sound, at least at some sound levels. Additional details on dual hearing protection devices and their operation can be found in U.S. Provisional patent application with Ser. No. 62/909,989, filed on Oct. 3, 2019.

Figure 5:
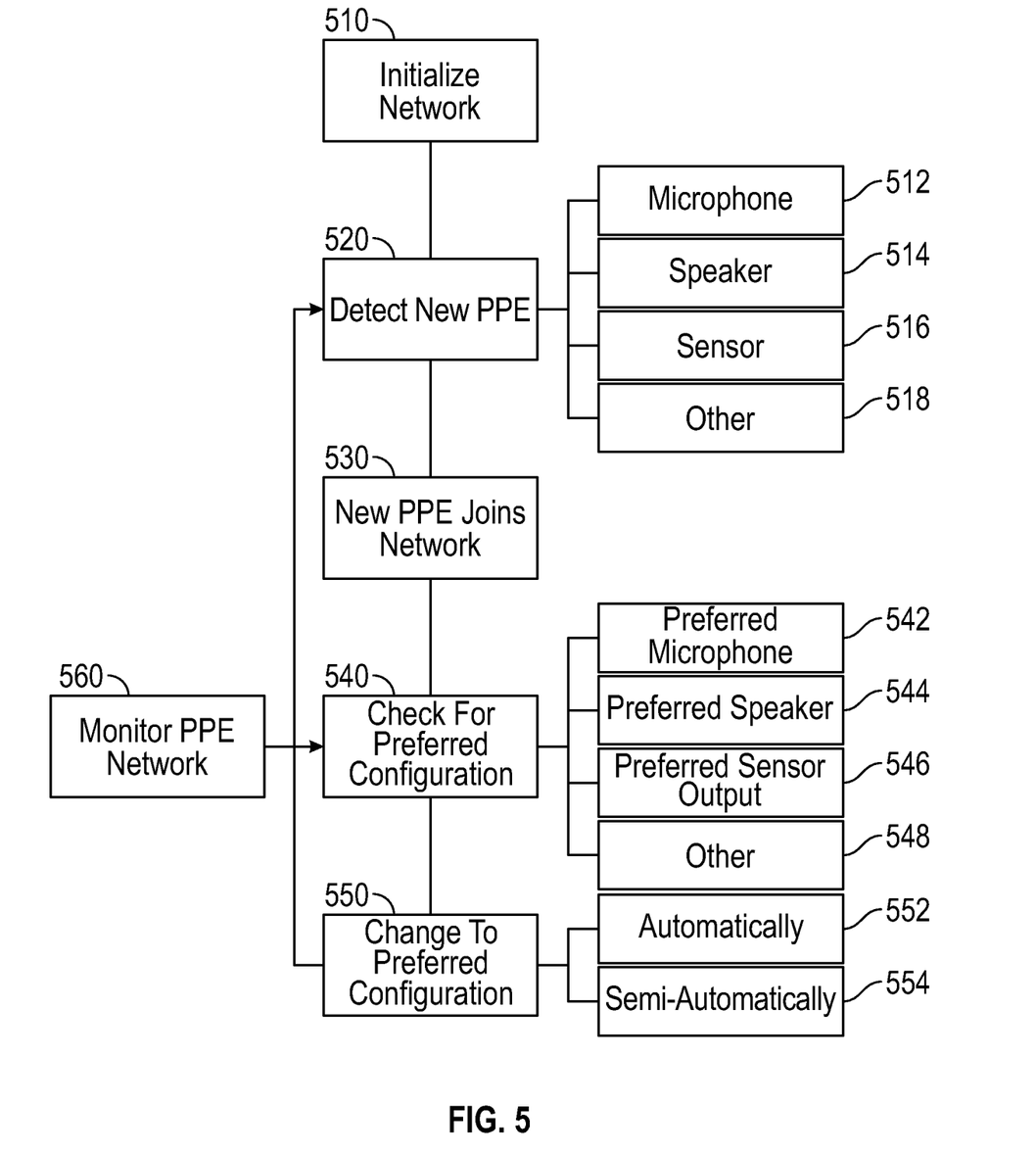
FIG. 5 illustrates a method of selecting a preferred signal routing arrangement in accordance with embodiments herein.

FIG. 5 illustrates a method of adapting communication signal routing in embodiments herein. Method 500 may be useful for a control unit in environments where a worker needs to change, add or remove PPE articles during daily operations, such as those described above in FIG. 3, for example. Method 500 is implemented, in one embodiment, in a control unit associated with a worker. The control unit may be worn by a wearer, and enabled to set up a wireless network that can be joined by other PPE devices. The network is a wireless network, in some embodiments. The network may utilize WiFi technology, Bluetooth, Zigbee, NFMI, or other suitable wireless technologies. However, it is also expressly contemplated that some PPE devices may connect to the control device using a wired connection. The control device may be the only device in a PPE network that communicates with other worker's PPE articles, or other worker's control devices. While many PPE devices may have two-way communication technology, or other wireless communication technology, a control unit may turn off said functionality upon the PPE article joining the network.

In block 510, a network is initialized by the control unit. The network is a wireless network, in one embodiment. However, the control unit may be configured to accept at least some wired connections to PPE articles, sensors, other communication devices, etc.

In block 520, a new PPE article is detected. For example, when a control unit creates a network, it may 'listen' or search for join requests, from personal protective equipment articles. In some embodiments, the PPE article detects the network and sends a transmission request to join the network, which can be accepted or rejected by the control unit. Other configurations may also be suitable, however, such as the PPE sending an active request. In another embodiment, the new PPE article may be detectable as soon as the PPE article is turned on, for example. For example, using Bluetooth® or other suitable technology, an enabled device can be detected by a network once it is turned on and the Bluetooth®, or other technology, is suitably active. Alternatively, detecting a new PPE article may include the PPE article detecting the network and requesting to join.

When the PPE article is detected, as illustrated in FIG. 5, information about the PPE article's functionality may be provided. However, it is also expressly contemplated that such information may be retrieved by the control unit from a database based on a detected make and model of the PPE article, or that the information may not be retrieved until after the PPE device joins the network.

The detected PPE article may have known functionality. For example, the PPE may have at least one microphone 512, for picking up speech from a wearer, at least one speaker 514, for delivering sound to a wearer, at least one sensor 516, for detecting information about a wearer, the PPE function, or the environment, and other functionality 518.

In block 530, the PPE article joins the network. Joining a network may be facilitated by the control unit and may require an authentication In block 540, a preferred configuration for the PPE is determined. The preferred configuration may include preferred signal routing within the network as well as preferred device functionality. For example, if both in-ear and over-ear hearing protection units are detected, a dual mode hearing protection may be enabled, and the devices adjusted accordingly. Concerning preferred signal routing, the control unit will select a preferred microphone 542 for picking up speech from a wearer and a preferred speaker 544 for delivering incoming audio to the wearer. Additionally, preferred sensory output 546 may be selected for the new PPE based whether other PPE articles are already collecting said sensory information. Avoiding duplicative sensory collection may both avoid duplicative data storage as well as preserve battery. Preferred microphone 542 and speaker 544 selections may be made based on a number of factors, including preserving signal fidelity, signal to noise ratio, audio quality and interference from other PPE devices or environmental conditions, such as wind interference. Additionally, preferred microphone 542 and speaker 544 selections may be made on device parameters, such as remaining battery life, etc. While determining a preferred configuration is illustrated in FIG. 5 as occurring after a device joins the network, it is also expressly contemplated that a preferred configuration may be determined as soon as a PPE device is detected and identified, in block 520. Other arrangements of the steps of method 500 are also contemplated.

In block 550, control unit changes device parameters for any affected devices within the network. For example, as functionality of the incoming PPE device is activated, similar functionality in other devices needs to be deactivated to avoid interferences. As indicated in block 552, the change may occur automatically and seamlessly such that a wearer's audio experience is substantially uninterrupted. However, the change may also occur semi-automatically—for example, the control unit may indicate that a new device is available and a preferred signal routing is also available. The switch may not occur until a user approves of the switch, or a period of time may be offered until the switch automatically occurs. For example, the control unit may provide an audible indication over an existing audio channel, or may provide haptic feedback through one or more affected devices. If a device with a heads-up, or other display, is detected within the network, a notification may be provided.

In block 560, the PPE network is monitored by the control unit. Monitoring may include monitoring PPE device functionality, and the method may at least partially repeat based on changing device parameters. For example, if a low battery is detected, the control unit may switch to a device that can provide similar functionality, even if at a reduced quality level, to preserve battery level of necessary PPE devices. Control unit may also keep track of, and note, when a worker switches away from a preferred functionality. For example, if a particular wearer does not like a boom microphone, they may always switch to a different microphone functionality. Control unit may store such information and select a less preferred signal routing configuration, from an audio quality standpoint, based on user preference. Additionally, as illustrated in FIG. 5, monitoring a PPE network can also include actively or passively monitoring for a new PPE device that may be ready to join.

FIG. 6A-6F illustrate different combinations of PPE articles that a worker may wear in embodiments herein. While FIGS. 6A-6F illustrate some potential combinations of PPE that a worker may need, it is expressly contemplated that other configurations of PPE articles may be worn by workers in other environments. For example, fall protection devices, fire suppression gear, helmets, goggles, face shields, gloves, or hoods may also have sensory output as well as speakers, microphones or other functionality.

Additionally, as described above with respect to FIG. 3, it is expressly contemplated that a worker 600 may switch between the configurations of FIGS. 6A-6F during a workday.

Figure 6A:
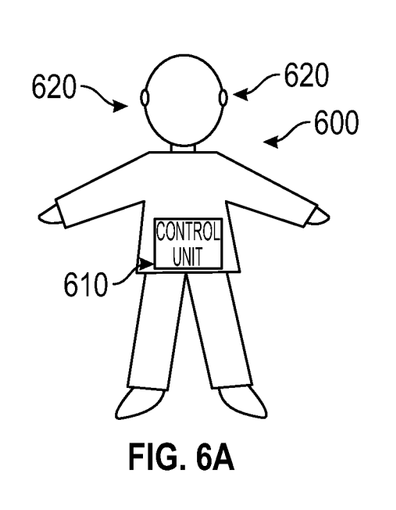
FIG. 6A-6F illustrate different combinations of PPE articles that a worker may wear in embodiments herein.
Figure 6B:
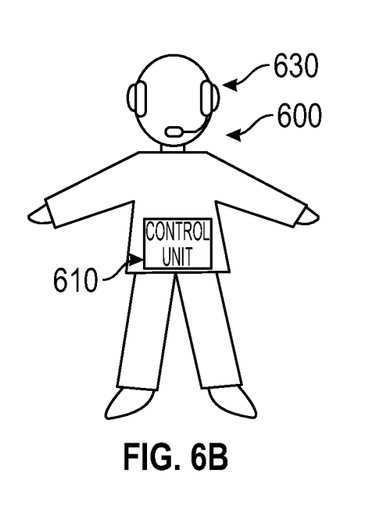
Figure 6C:
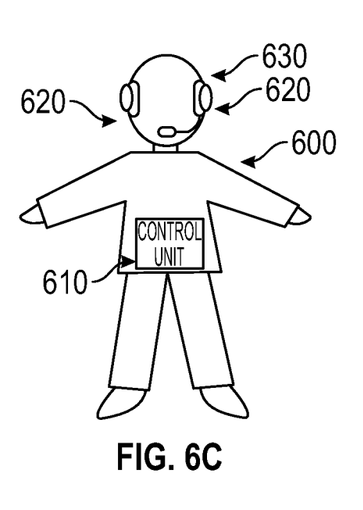
Figure 6D:
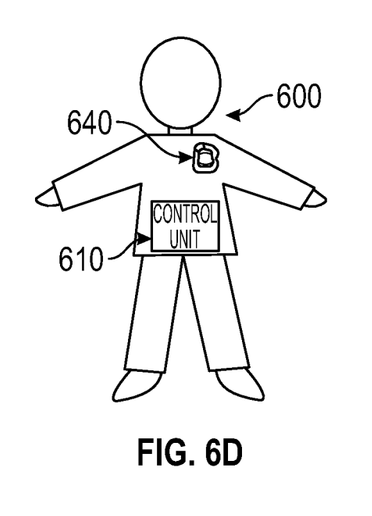
Figure 6E:
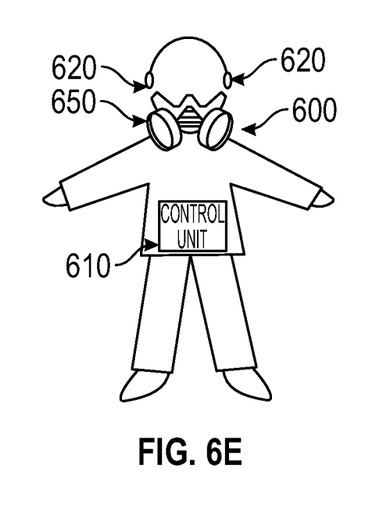
Figure 6F:
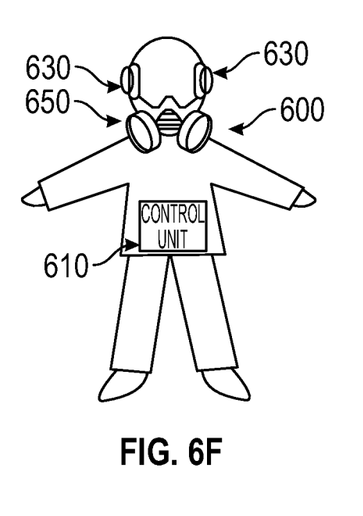

In FIG. 6A, a worker 600 is wearing a control device 610 and a pair of in-ear hearing protection devices. In FIG. 6B, worker 600 is wearing over-ear hearing protection device 630 and control unit 610. In FIG. 6C, worker 600 is wearing both in-ear protection devices 620 and over-ear hearing protection 630, which may be in dual hearing mode based on a signal from control unit 610. In FIG. 6D, worker 600 is wearing a shoulder microphone 640 and control unit 610. In FIG. 6E, worker 600 is wearing in-ear hearing protection devices 620 as well as a respirator 650, both controlled by control unit 610. In FIG. 6F, worker 600 is wearing over-ear hearing protection device 630 as well as respirator 650 and control unit 610.

Figure 7:
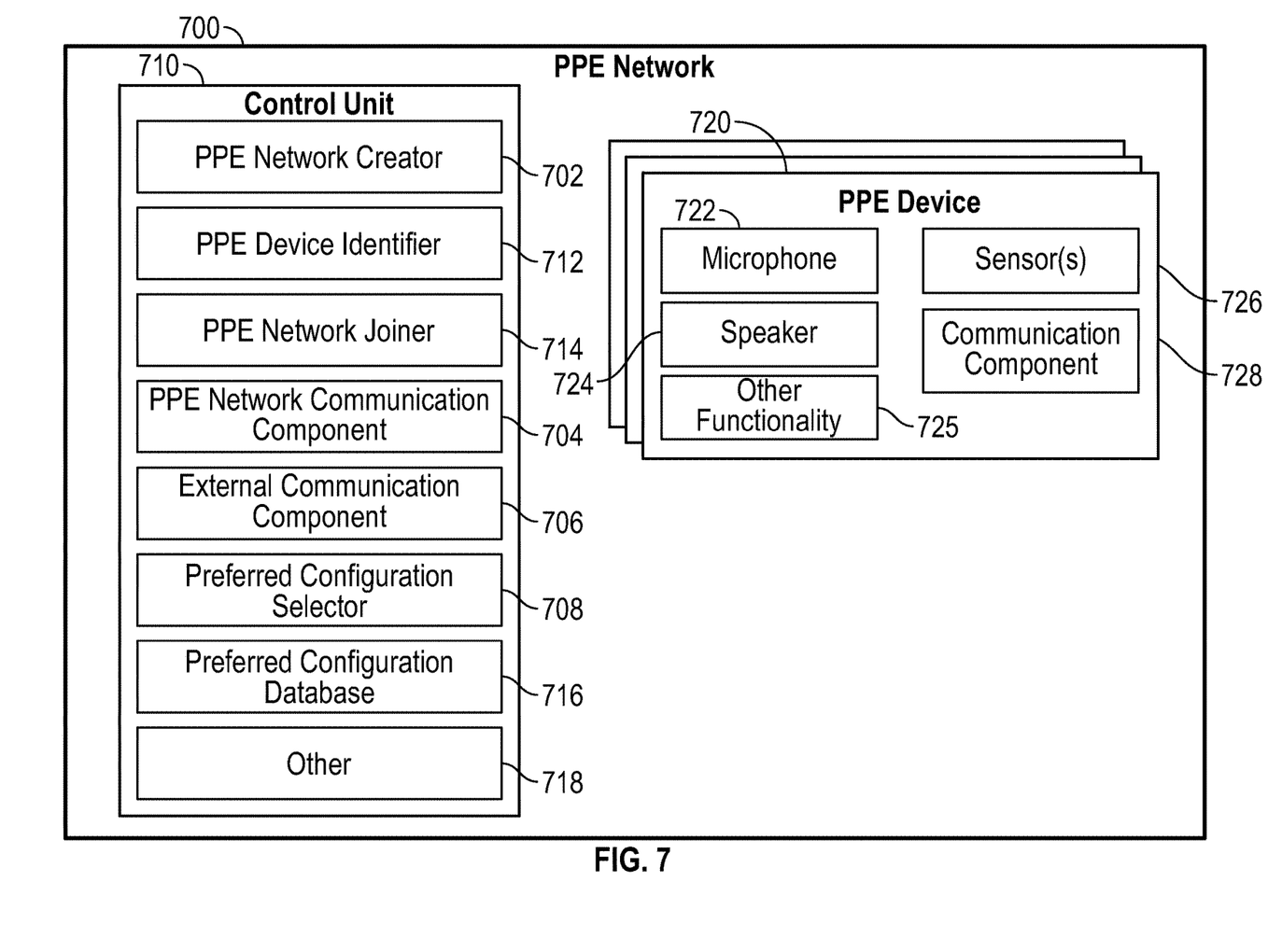
FIG. 7 illustrates a block diagram of a PPE network in accordance with embodiments herein.

FIG. 7 illustrates an example block diagram of a PPE network in accordance with embodiments herein. PPE network 700 may be associated with a worker wearing one or more PPE devices 720, as well as a control unit 710. PPE devices 720 may include, but are not limited to: in-ear protection devices, over-ear protection devices, helmets, face shields, face masks, respirators, shoulder microphones, fall protection gear, hoods or any other personal protective equipment that has any of a microphone 722, a speaker 724, sensor 726, or other functionality 725.

Control unit 710 is intended to be worn or carried by a worker as they move through a worksite or work environment. Control unit, using a PPE network creator 702, creates the PPE network, which is a wireless network and may operate using WIFI, Bluetooth®, NFC, NFMI, Zigbee, or any other suitable wireless communication protocol. PPE network 700 extends far enough that PPE devices 720 can join network when worn by a worker. PPE network may be limited in range such that PPE devices associated with another worker are not accidentally joined to PPE network 700. In some embodiments, there is a pairing period so that new PPE articles can only join within a certain time period of the control unit powering on, for example, to limit accidental joining. For example, NFMI networks are limited to about 2 meters. Artificial limitations on network range may be placed, for example, by detecting a signal strength of a network is less than a required threshold.

PPE device identifier 712 identifies a PPE device 720 either before it joins a network, in some embodiments, or when it joins the network, facilitated by PPE network joiner

714, in other embodiments. Identifying a PPE device 720 may include an authentication step to ensure that PPE device 720 can join the network, for example based on range from control unit 710 or other suitable criteria. Identifying a PPE device 720 may also include retrieving information about PPE device 720 either from PPE device 720 itself or from a database (not shown). PPE device information may include information about whether or not components 722, 724, 726 are present, and what quality level each offers.

PPE network communication component 704 may exchange device parameter information with PPE device 720, using communication component 728. Device parameter information may include a command to activate/deactivate or to change an operational parameter for any of components 722, 724, 726 or other device functionality 725. The command may be sent based on a preferred configuration selector 708, which determines preferred operation of devices 720, and preferred signal routing between control unit 710 and devices 720 by accessing a preferred configuration database 716 which may, based on known or received information about devices 720, have preferred signal routing patterns that preferred configuration selector 708 chooses from.

Control unit 710 is also configured to receive incoming audio from a source external to the PPE network 700, and to send outgoing audio to a source external to the PPE network 700, using external network component 706. For example, a microphone 722 picks up speech from a wearer, and sends it to control unit 710, using communication component 728. Control unit 710 receives the communication through PPE network communication component 704, and provides it to an external source through an external communication component 706. External communication component may communicate with other control units, associated with other nearby or remote workers, using any number of suitable communication protocols including cellular, 2G, 3G, 4G, or 5G networks, wireless communication protocols, or any other suitable communication protocol.

A control unit for a worker wearing personal protective equipment is presented. The control unit includes a PPE network creator that, when activated, creates a network. The control unit also includes a PPE device identifier configured to detect a first PPE associated with the worker and a second PPE associated with the worker. The first PPE has a first speaker and a first microphone. The second PPE has a second speaker and a second microphone. The control unit also includes a PPE network joiner that facilitates the first and second PPE joining the network. The control unit also includes a preferred configuration selector that automatically selects a preferred speaker for the worker and a preferred microphone for the worker. The preferred speaker is the first or second speaker. The preferred microphone is the first or second microphone. The control unit also includes a network communication component that automatically communicates a first device parameter settings to the first PPE and a second device parameter settings to the second PPE. The first and second device parameter settings are based on the selected preferred speaker and microphone.

The control unit may be implemented such that the network is a personal area network.

The control unit may be implemented such that the network is a wireless network.

The control unit may be implemented such that the PPE device identifier detecting the first or second PPE associated with worker includes detecting that the first or second PPE is within range of the control unit.

The control unit may be implemented such that the preferred configuration selector selects the preferred speaker and the preferred microphone based on a detected type of the first and second PPE.

The control unit may be implemented such that the first PPE is selected from a group consisting of: an in-ear hearing protector, an over-ear hearing protector, a hood, a face shield, a face mask, a respirator, and a shoulder microphone.

The control unit may be implemented such that the second PPE is selected from a group consisting of: an in-ear hearing protector, an over-ear hearing protector, a hood, a face shield, a face mask, a respirator, and a shoulder microphone.

The control unit may be implemented such that one of the preferred speaker and the preferred microphone is selected based on a detected brand or model of the first and second PPE.

The control unit may be implemented such that the preferred speaker and preferred microphone are selected based on reducing expected interference, preserving audio fidelity, or remaining battery life.

The control unit may be implemented such that it also includes an external communication component that receives incoming audio from a source outside of the network and sends outgoing audio from the microphone to the source.

The control unit may be implemented such that the preferred configuration selector selects a configuration at least in part by referencing a database of PPE data.

The control may be implemented such that the database of PPE data includes a look-up table of preferred microphone and preferred speakers to select based on the first and second PPE.

The control unit may be implemented such that the first device parameter settings include a sensor output setting.

The control unit may be implemented such that the first device parameter settings include a device functionality setting.

The control unit may be implemented such that the first PPE is an in-ear hearing protection device and the second PPE is an over-ear hearing protection device. The first device parameter settings and the second device parameter settings include settings corresponding to the first and second PPE operating in a dual hearing protection mode.

The control unit may be implemented such that communicating the first and second device parameter settings includes instructions to automatically implement the first and second device parameter settings.

The control unit may be implemented such that automatically implementing the first and second device parameter settings include implementing such that the worker experiences a seamless transition.

The control unit may be implemented such that the first PPE is a hearing protection device, the second PPE is a respirator. Incoming audio is routed to the hearing protection device. A speaker of the respirator is turned off.

The control unit may be implemented such that the first PPE is a hearing protection device, the second PPE is a shoulder microphone. Incoming audio is routed to the hearing protection device. A speaker of the shoulder microphone is turned off.

A method for controlling parameters of personal protective equipment is presented that includes detecting a new PPE device joining a network. The network is controlled by a control unit. The method also includes identifying, using the control unit, a communication feature of the new PPE device. The communication feature is a microphone or a speaker. The method also includes automatically comparing, using a comparison module of the control unit, the identified communication feature to a current signal routing configuration within the network. The current signal routing configuration includes a current microphone that captures speech and a current speaker that broadcasts incoming sound. The method also includes determining, based on the comparison, that the communication feature of the new PPE device is preferred over either the current microphone or the current speaker. The method also includes adjusting device parameters, by sending a communication from the control unit to each of the new and current PPE, for the current PPE and the new PPE such that a preferred speaker broadcasts incoming sound and a preferred microphone captures speech.

The method may be implemented such that adjusting device parameters includes automatically sending a current PPE configuration command to the current PPE and a new PPE configuration command to the new PPE to change device parameters.

The method may be implemented such that the current PPE and new PPE change configurations automatically based on the received configuration commands. The adjustment is substantially seamless.

The method may be implemented such that the current PPE is selected from the group consisting of: an in-ear hearing protector, an over-ear hearing protector, a hood, a face shield, a face mask, a respirator and a shoulder microphone.

The method may be implemented such that the new PPE is selected from the group consisting of: an in-ear hearing protector, an over-ear hearing protector, a hood, a face shield, a face mask, a respirator, and a shoulder microphone The method may be implemented such that the preferred speaker and the preferred microphone is selected based on a detected brand or model of the current and new PPE.

The method may be implemented such that the preferred speaker and preferred microphone are selected based on reducing expected interference, preserving audio fidelity, or remaining battery life.

The method may be implemented such that the current PPE is an in-ear hearing protector, the new PPE is an over-ear hearing protector. The current PPE configuration command and the new PPE configuration command include the current and new PPE entering a dual hearing protection mode.

The method may be implemented such that the preferred microphone is a boom microphone of the over-ear hearing protector.

The method may be implemented such that the current PPE is a shoulder microphone. The new PPE is a hearing protector. The preferred speaker is a hearing protector speaker. The current PPE configuration command includes deactivation of a shoulder microphone speaker.

The method may be implemented such that it includes monitoring the network for new PPE.

The method may be implemented such that it also includes initializing the network, which is a wireless network.

The method may be implemented such that the network is a personal area network.

The method may be implemented such that it also includes detecting that either the current or the new PPE device has left the network, determining a new preferred speaker and a new preferred microphone, and adjusting device parameters to cause the new preferred speaker to broadcast incoming sound and the new preferred microphone to receive speech.

A personal protection equipment network is presented that includes a first device with a first microphone and a first speaker and a second device with a second microphone and a second speaker, and a control unit. The control unit initiates the personal protection equipment network and joins the first and second devices to the network, joins the first and second devices to the network, selects a preferred microphone based on a comparison of the first and second microphones, selects a preferred speaker based on a comparison of the first and second microphones, and sends a control command to the first and second devices such that the preferred microphone and speaker are enabled. The first device and the second device are both personal protection equipment devices.

The personal protection equipment network may be implemented such that the first speaker is the preferred speaker, and the control command disables the second speaker.

The personal protection equipment network may be implemented such that the control unit also receives an incoming sound signal from outside the network and provides the incoming sound signal to the preferred speaker.

The personal protection equipment network may be implemented such that the control unit also receives a speech signal from the preferred microphone and provides it to a source outside the network.

The personal protection equipment network may be implemented such that the first and second devices are different, and each is selected from a group consisting of: an in-ear hearing protector, an over-ear hearing protector, a hood, a face shield, a face mask, a respirator, and a shoulder microphone.

The personal protection equipment network may be implemented such that the preferred speaker and the preferred microphone is selected based on a detected brand or model of the first and second device.

The personal protection equipment network may be implemented such that the preferred speaker and preferred microphone are selected based on reducing expected interference, preserving audio fidelity, or remaining battery life.

The personal protection equipment network may be implemented such that the first device is an in-ear hearing protector, the second device is an over-ear hearing protector. The current PPE configuration command and the new PPE configuration command include the current and new PPE entering a dual hearing protection mode.

The personal protection network may be implemented such that the preferred microphone is a boom microphone of the over-ear hearing protector.

The personal protection network may be implemented such that the first device is a hearing protection device. The preferred microphone is the first microphone.

The personal protection network may be implemented such that the first device is a respirator. The second speaker is the preferred speaker.

EXAMPLES

FIGS. 8A-8F illustrate different preferred signal routing arrangements in different example operations herein. FIGS. 8A-8F do not illustrate an exhaustive range, however. For example, throat microphones and bone conducted microphones and speakers are some additional example PPE articles not illustrated herein, but which may be part of a personal protective equipment network.

Example 1

Figure 8A:
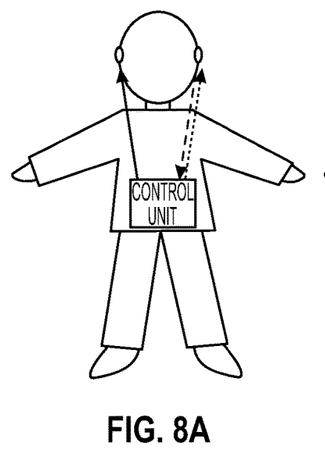
FIGS. 8A-8F illustrate different preferred signal routing arrangements in accordance with embodiments herein.

Example 1, illustrated in FIG. 8A, includes an in-ear headset worn by a user with at least some parameters controlled by a control unit. Incoming communications are provided to the in-ear headsets, with a left audio signal sent to the left in-ear plug, a right audio sent to the right in-ear plug. Outbound speech is recorded by the left in-ear plug microphone and provided to the control unit, which transfers it out of the PPE network.

Example 2

Figure 8B:
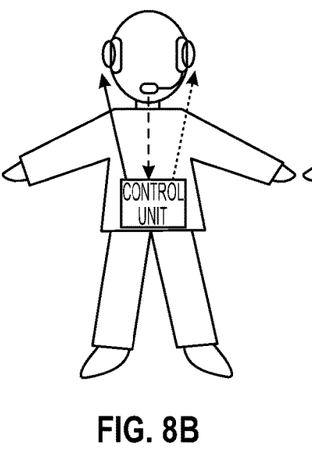

Example 2, illustrated in FIG. 8B, includes a control unit and an over-ear headset. An audio left signal is sent to the left earmuff, and an audio right signal is sent to the right ear muff. Outbound speech is recorded by a boom microphone and transmitted to the control unit, which transfers it out of the PPE network.

Example 3

Figure 8C:
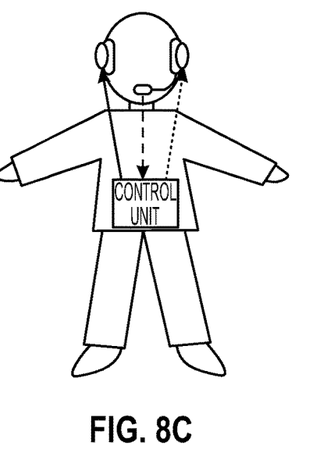

Example 3, illustrated in FIG. 8C, includes both in-ear hearing devices and an over-ear hearing protection device, operating in a dual hearing protection mode as dictated by a control unit. Incoming communication is transmitted directly to the in-ear units, a left audio signal to a left in-ear unit and a right audio signal to a right in-ear unit. Outgoing speech is recorded by the boom microphone of the over-ear hearing protection device.

Example 4

Figure 8D:
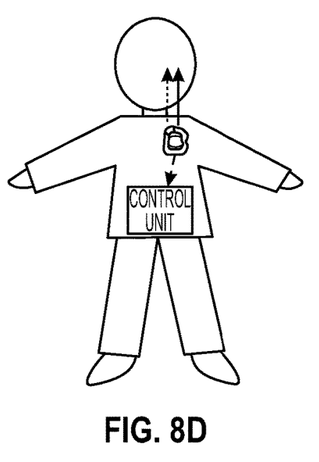

Example 4, illustrated in FIG. 8D, includes a shoulder microphone and a control unit. The control unit sends incoming communications to the shoulder microphone, which broadcasts them for the wearer. Outbound speech is recorded by the shoulder microphone and provided to the control unit, which sends it externally.

Example 5

Figure 8E:
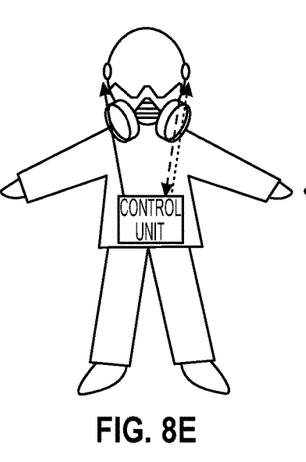

Example 5, illustrated in FIG. 8E, includes a pair of in-ear protection devices and a respirator. Because the respirator is known to have poor microphone quality, outgoing speech is recorded by the left in-ear microphone and provided to the control unit. Incoming audio is provided from the control unit, with a left audio signal to the left in-ear piece, and a right audio signal to the right in-ear piece.

Example 6

Figure 8F:
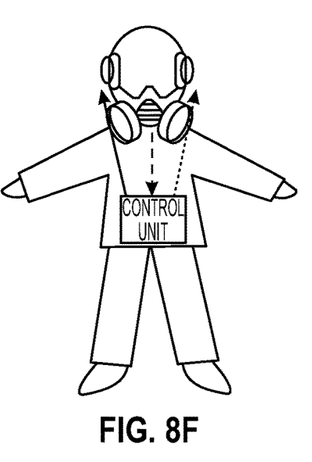

Example 6, illustrated in FIG. 8F, includes a pair of in-ear hearing protection devices and an over-ear hearing protection device, operating in a dual hearing protection mode as dictated by the control unit, as well as a respirator. Outgoing audio is provided by a microphone in the respirator unit to the control unit. Incoming audio is provided from the control unit to the over-ear hearing protection device, which processes it through the dual hearing protection mode, with a left audio signal sent to the left ear muff and a right audio signal sent to the right ear muff.

What is claimed is:

1. A control unit for a worker wearing personal protective equipment, the control unit comprising:
    a PPE network creator that, when activated, creates a network;
    a PPE device identifier configured to detect a first PPE associated with the worker and a second PPE associated with the worker, wherein the first PPE has a first speaker and a first microphone, and wherein the second PPE has a second speaker and a second microphone;
    a PPE network joiner that facilitates the first and second PPE joining the network;
    a preferred configuration selector that automatically selects a preferred speaker for the worker and a preferred microphone for the worker, wherein the preferred speaker is the first or second speaker, and wherein the preferred microphone is the first or second microphone; and
    a network communication component that automatically communicates a first device parameter settings to the first PPE and a second device parameter settings to the second PPE, wherein the first and second device parameter settings are based on the selected preferred speaker and microphone.

2. The control unit of claim 1, wherein the network is a personal area network.

3. The control unit of claim 1, wherein the PPE device identifier detecting the first or second PPE associated with worker comprises detecting that the first or second PPE is within range of the control unit.

4. The control unit of claim 1, wherein the preferred configuration selector selects the preferred speaker and the preferred microphone based on a detected type of the first and second PPE.

5. The control unit of claim 4, wherein the first PPE is selected from a group consisting of: an in-ear hearing protector, an over-ear hearing protector, a hood, a face shield, a face mask, a respirator, and a shoulder microphone.

6. The control unit of claim 4, wherein the preferred speaker and preferred microphone are selected based on reducing expected interference, preserving audio fidelity, or remaining battery life.

7. The control unit of claim 1, and further comprising:
    an external communication component that receives incoming audio from a source outside of the network and sends outgoing audio from the microphone to the source.

8. The control unit of claim 1, wherein communicating the first and second device parameter settings includes instructions to automatically implement the first and second device parameter settings.

9. The control unit of claim 1, wherein the first PPE is a hearing protection device, the second PPE is a respirator; and wherein incoming audio is routed to the hearing protection device, and wherein a speaker of the respirator is turned off.

10. A method for controlling parameters of personal protective equipment, the method comprising:
    detecting a new PPE device joining a network, wherein the network is controlled by a control unit;
    identifying, using the control unit, a communication feature of the new PPE device, wherein the communication feature is a microphone or a speaker;
    automatically comparing, using a comparison module of the control unit, the identified communication feature to a current signal routing configuration within the network, wherein the current signal routing configuration comprises a current microphone that captures speech and a current speaker that broadcasts incoming sound;
    determining, based on the comparison, that the communication feature of the new PPE device is preferred over either the current microphone or the current speaker; and adjusting device parameters, by sending a communication from the control unit to each of the new and current PPE, for the current PPE and the new PPE such that a preferred speaker broadcasts incoming sound and a preferred microphone captures speech.

11. The method of claim 10, wherein adjusting device parameters comprises automatically sending a current PPE configuration command to the current PPE and a new PPE configuration command to the new PPE to change device parameters.

12. The method of claim 11, wherein the current PPE and new PPE change configurations automatically based on the received configuration commands, and wherein the adjustment is substantially seamless.

13. The method of any of claim 10, and further comprising:
monitoring the network for new PPE.

14. The method of claim 10, and further comprising:
detecting that either the current or the new PPE device has left the network;
determining a new preferred speaker and a new preferred microphone; and
adjusting device parameters to cause the new preferred speaker to broadcast incoming sound and the new preferred microphone to receive speech.

15. A personal protection equipment network comprising:
a first device with a first microphone and a first speaker;
a second device with a second microphone and a second speaker; and
a control unit that:
initiates the personal protection equipment network and joins the first and second devices to the network;

joins the first and second devices to the network;
selects a preferred microphone based on a comparison of the first and second microphones;
selects a preferred speaker based on a comparison of the first and second microphones; and
sends a control command to the first and second devices such that the preferred microphone and speaker are enabled; and
wherein the first device and the second device are both personal protection equipment devices.

16. The personal protection equipment network of claim 15, wherein the first speaker is the preferred speaker, and the control command disables the second speaker.

17. The personal protection equipment network of claim 16, wherein the first device is an in-ear hearing protector, the second device is an over-ear hearing protector, and wherein the current PPE configuration command and the new PPE configuration command comprise the current and new PPE entering a dual hearing protection mode.

18. The personal protection network of claim 16, wherein the first device is a hearing protection device, and wherein the preferred microphone is the first microphone.

19. The personal protection network of claim 16, wherein the first device is a respirator, and wherein the second speaker is the preferred speaker.

20. The personal protection equipment network of claim 15, wherein the preferred speaker and preferred microphone are selected based on reducing expected interference, preserving audio fidelity, or remaining battery life.

* * * * *